(12) United States Patent
Sawhney et al.

(10) Patent No.: US 11,377,498 B2
(45) Date of Patent: *Jul. 5, 2022

(54) EXTRA LUMINAL SCAFFOLD

(71) Applicant: Incept, LLC, Lexington, MA (US)

(72) Inventors: Amarpreet S. Sawhney, Lexington, MA (US); Farhad Khosravi, Los Altos Hills, CA (US); Patrick Campbell, Belmont, MA (US)

(73) Assignee: Incept, LLC, Lexington, MA (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/721,085

(22) Filed: Dec. 19, 2019

(65) Prior Publication Data
US 2020/0207860 A1    Jul. 2, 2020

Related U.S. Application Data

(63) Continuation of application No. 15/520,877, filed as application No. PCT/US2015/057091 on Oct. 23, 2015, now Pat. No. 10,550,187.
(Continued)

(51) Int. Cl.
*A61F 2/82* (2013.01)
*C07K 16/28* (2006.01)
(Continued)

(52) U.S. Cl.
CPC .... *C07K 16/2833* (2013.01); *A61B 17/00491* (2013.01); *A61F 2/945* (2013.01); *A61K 38/1774* (2013.01); *A61K 45/06* (2013.01); *A61L 31/145* (2013.01); *A61M 25/104* (2013.01); *C07K 16/2803* (2013.01); *C07K 16/2863* (2013.01); *A61B 2017/00654* (2013.01); *A61B 2017/00893* (2013.01); *A61B 2017/00898* (2013.01); *A61F 2/82* (2013.01); *A61F 2002/041* (2013.01); *A61F 2002/044* (2013.01); *A61F 2002/045* (2013.01);
(Continued)

(58) Field of Classification Search
CPC .................................. A61F 2/94; A61F 2/945
USPC ................................................ 623/1.42–1.48
See application file for complete search history.

(56) References Cited

U.S. PATENT DOCUMENTS 3,640,741 A    2/1972  Etes
3,865,108 A    2/1975  Hartop
(Continued)

FOREIGN PATENT DOCUMENTS

WO    2006031358    3/2006
WO    2006031388    3/2006
(Continued)

OTHER PUBLICATIONS

Ikeno et al., "Novel Percutaneous Adventitial Drug Delivery System For Regional Vascular Treatment", Catheter Cardiovasc Interv, vol. 63(2):222-230 (Oct. 2004). (Abstract Only).
(Continued)

*Primary Examiner* — Suzette J Gherbi
(74) *Attorney, Agent, or Firm* — Christensen, Fonder, Dardi & Herbert PLLC; Peter S. Dardi; Diane E. Bennett

(57) ABSTRACT

Methods and devices for treating a luminal pathology affecting an anatomical lumen of a patient comprising forming, in situ, a continuous cohesive layer of covalently-crosslinked hydrogel in a luminal wall of the anatomical lumen.

23 Claims, 4 Drawing Sheets

Related U.S. Application Data

(60) Provisional application No. 62/068,351, filed on Oct. 24, 2014.

(51) Int. Cl.

| | | |
|---|---|---|
| *A61B 17/00* | (2006.01) | |
| *A61L 31/14* | (2006.01) | |
| *A61M 25/10* | (2013.01) | |
| *A61F 2/945* | (2013.01) | |
| *A61K 38/17* | (2006.01) | |
| *A61K 45/06* | (2006.01) | |
| *A61F 2/04* | (2013.01) | |
| *A61K 39/00* | (2006.01) | |

(52) U.S. Cl.
CPC ... *A61F 2002/048* (2013.01); *A61F 2002/823* (2013.01); *A61F 2210/0085* (2013.01); *A61F 2250/0067* (2013.01); *A61K 2039/505* (2013.01); *A61K 2039/507* (2013.01); *A61M 2025/105* (2013.01); *C07K 2317/24* (2013.01); *C07K 2317/55* (2013.01); *C07K 2317/565* (2013.01); *C07K 2317/73* (2013.01); *C07K 2317/76* (2013.01)

(56) References Cited

U.S. PATENT DOCUMENTS

| | | | |
|---|---|---|---|
| 3,992,562 A | 11/1976 | Denzinger et al. | |
| 4,002,173 A | 1/1977 | Manning et al. | |
| 4,014,335 A | 3/1977 | Arnold | |
| 4,207,893 A | 6/1980 | Michaels | |
| 4,741,872 A | 5/1988 | De Luca et al. | |
| 4,826,945 A | 5/1989 | Cohn et al. | |
| 4,938,763 A | 7/1990 | Dunn et al. | |
| 5,100,992 A | 3/1992 | Cohn et al. | |
| 5,160,745 A | 11/1992 | DeLuca et al. | |
| 5,210,392 A | 5/1993 | Labrot et al. | |
| 5,242,397 A | 9/1993 | Barath et al. | |
| 5,304,595 A | 4/1994 | Rhee et al. | |
| 5,324,775 A | 6/1994 | Rhee et al. | |
| 5,354,279 A | 10/1994 | Höfling | |
| 5,410,016 A | 4/1995 | Hubbell et al. | |
| 5,575,815 A * | 11/1996 | Slepian | A61L 31/145 600/36 |
| 5,674,192 A * | 10/1997 | Sahatjian | A61F 2/90 604/28 |
| 5,782,860 A | 7/1998 | Epstein et al. | |
| 5,791,085 A | 8/1998 | Szmidt et al. | |
| 6,149,931 A | 11/2000 | Schwartz et al. | |
| 6,302,870 B1 | 10/2001 | Jacobsen et al. | |
| 6,371,975 B2 | 4/2002 | Cruise et al. | |
| 6,451,240 B1 | 9/2002 | Sherman et al. | |
| 6,547,803 B2 | 4/2003 | Seward et al. | |
| 6,682,555 B2 * | 1/2004 | Cioanta | A61B 18/04 604/101.03 |
| 6,689,148 B2 * | 2/2004 | Sawhney | A61B 17/12022 606/193 |
| 6,818,018 B1 | 11/2004 | Sawhney | |
| 6,958,212 B1 | 10/2005 | Hubbell et al. | |
| 6,991,804 B2 | 1/2006 | Helmus et al. | |
| 7,127,284 B2 | 10/2006 | Seward | |
| 7,129,210 B2 | 10/2006 | Lowinger et al. | |
| 7,141,041 B2 | 11/2006 | Seward | |
| 7,220,270 B2 * | 5/2007 | Sawhney | A61B 17/12022 606/193 |
| 7,648,713 B2 * | 1/2010 | Sawhney | A61K 9/0085 424/426 |
| 7,744,584 B2 | 6/2010 | Seward et al. | |
| 7,776,063 B2 * | 8/2010 | Sawhney | A61K 9/0024 606/193 |
| 7,780,980 B2 * | 8/2010 | Sawhney | A61K 9/0085 424/443 |
| 7,914,541 B2 * | 3/2011 | Sawhney | A61M 31/00 606/139 |
| 8,465,752 B2 | 6/2013 | Seward | |
| 8,721,590 B2 | 5/2014 | Seward et al. | |
| 8,740,849 B1 | 6/2014 | Fischell et al. | |
| 8,771,252 B2 | 7/2014 | Gelfand et al. | |
| 8,876,759 B2 | 11/2014 | Crank | |
| 8,945,045 B2 | 2/2015 | Lund et al. | |
| 8,975,233 B2 | 3/2015 | Stein et al. | |
| 9,498,557 B2 * | 11/2016 | Pathak | A61L 24/0031 |
| 10,550,187 B2 * | 2/2020 | Sawhney | A61F 2/945 |
| 2002/0091299 A1 * | 7/2002 | Silverman | A61F 2/04 600/29 |
| 2003/0059463 A1 * | 3/2003 | Lahtinen | A61L 27/54 424/450 |
| 2003/0078562 A1 | 4/2003 | Makower et al. | |
| 2004/0086479 A1 | 5/2004 | Grinstaff et al. | |
| 2004/0131582 A1 | 7/2004 | Grinstaff et al. | |
| 2005/0277864 A1 * | 12/2005 | Haffner | A61L 27/50 604/8 |
| 2006/0084759 A1 * | 4/2006 | Calabro | C08B 37/0072 525/54.1 |
| 2009/0017097 A1 | 1/2009 | Sawhney et al. | |
| 2009/0142309 A1 * | 6/2009 | Calabro | C12N 5/0068 424/93.7 |
| 2011/0142936 A1 | 6/2011 | Campbell et al. | |
| 2011/0270216 A1 | 11/2011 | Rykhus et al. | |
| 2012/0016465 A1 | 1/2012 | Koopman | |
| 2012/0071865 A1 | 3/2012 | Jarrett et al. | |
| 2014/0052168 A1 * | 2/2014 | Sawhney | A61K 6/19 606/192 |
| 2014/0058356 A1 | 2/2014 | Chu et al. | |
| 2014/0093473 A1 * | 4/2014 | Hauser | A61L 27/22 424/78.17 |
| 2014/0303569 A1 | 10/2014 | Seward et al. | |
| 2014/0343476 A1 * | 11/2014 | Penhasi | A61F 9/00781 604/8 |
| 2015/0203820 A1 * | 7/2015 | Wang | A61K 35/28 424/93.7 |
| 2015/0224289 A1 | 8/2015 | Seward | |
| 2015/0352014 A1 * | 12/2015 | Lamport | A61J 15/0011 604/528 |
| 2016/0024461 A1 * | 1/2016 | Sun | C08J 3/075 435/68.1 |
| 2016/0106587 A1 | 4/2016 | Jarrett et al. | |
| 2017/0007324 A1 * | 1/2017 | Kadamus | A61B 5/0036 |
| 2017/0049696 A1 * | 2/2017 | Chevrier | A61K 9/19 |
| 2017/0157035 A1 | 6/2017 | Seward et al. | |
| 2017/0273827 A1 | 9/2017 | Prausnitz et al. | |
| 2017/0340560 A1 | 11/2017 | Yamamoto et al. | |
| 2018/0021045 A1 * | 1/2018 | Deaton | A61B 17/12113 623/1.15 |
| 2018/0085496 A1 * | 3/2018 | Fahmy | A61L 27/20 |
| 2020/0107821 A1 * | 4/2020 | Mylonakis | C08L 71/02 |

FOREIGN PATENT DOCUMENTS

| | | |
|---|---|---|
| WO | 2007001926 | 1/2007 |
| WO | 2007005249 | 1/2007 |

OTHER PUBLICATIONS

Lovich et al., "Arterial Heparin Deposition: Role Of Diffusion Convection, And Extravascular Space", American Physiological Society, 7 Pages (1998).

"Blowfish® Transbronchial Micro-Infusion Device" Mercator MedSystems, 2 Pages (2017).

"Blowfish® Transbronchial Micro-Infusion Device" 510(K) Notification, Mercator MedSystems, Section 5, 6 Pages (Jul. 2, 2013).

"Bullfrog® Micro-Infusion Device" Mercator MedSystems 3 Pages (2017).

"Bullfrog® Micro-Infusion Device" 510(K) Notification, Mercator MedSystems, 5 Pages (Apr. 15, 2016).

\* cited by examiner

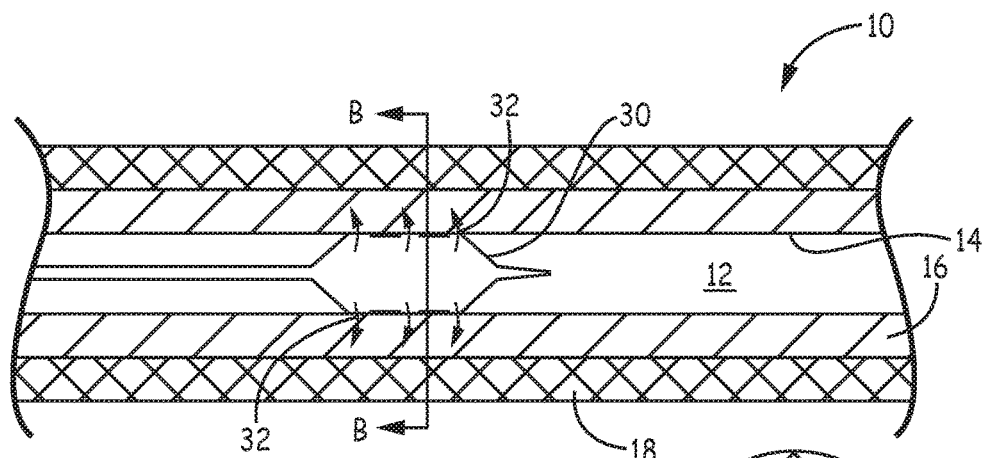
FIG. 3A
FIG. 3C
FIG. 3B
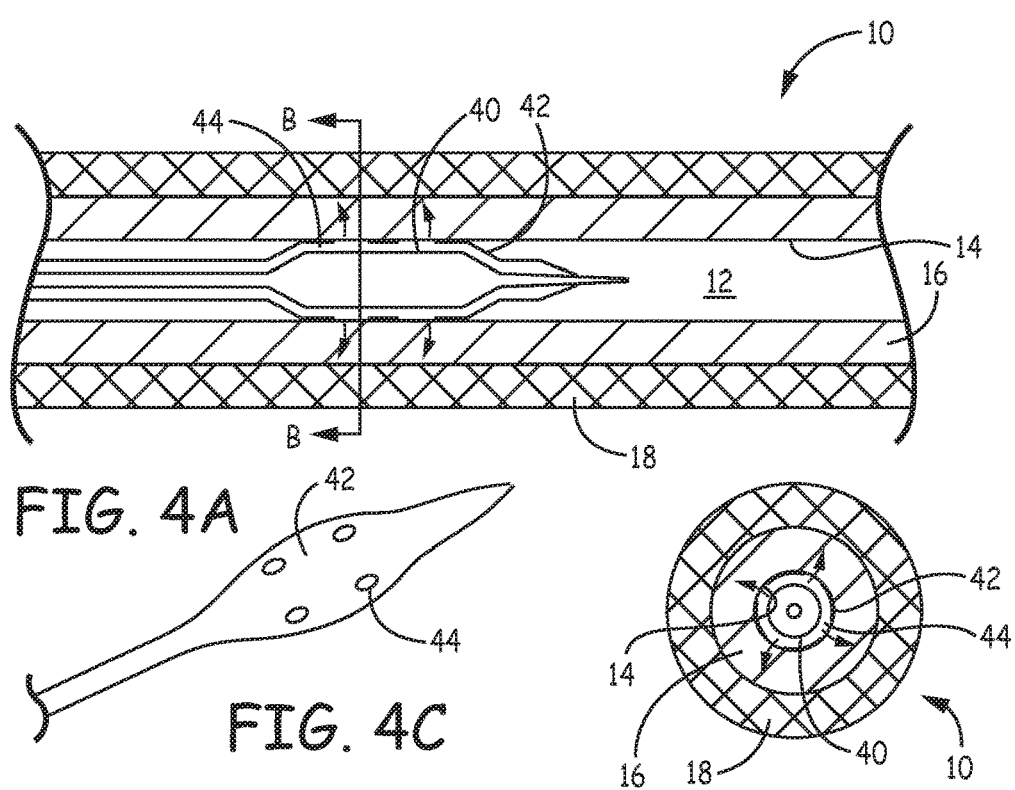
FIG. 4A
FIG. 4C
FIG. 4B

EXTRA LUMINAL SCAFFOLD

CROSS REFERENCE TO RELATED APPLICATIONS

This application is a continuation of U.S. patent application Ser. No. 15/520,877 filed Apr. 21, 2017, which claims priority to PCT Application No. PCT/US2015/057091 filed Oct. 23, 2015, and U.S. Provisional Application No. 62/068,351 filed Oct. 24, 2014, all of which are hereby incorporated herein by reference.

TECHNICAL FIELD

The technical field is related to bioeffective drugs and compositions for treating the body, and includes surgical tools and pharmaceutically acceptable implant systems comprising hydrogels that support the wall of an anatomical cavity or deliver a drug to the wall of an anatomical cavity.

BACKGROUND

Implants that deliver drugs over time in a therapeutically effective dosage are useful in many fields. The science of controlled drug release is diverse from a standpoint of both range of scientific disciplines it encompasses and the range of its applications.

SUMMARY

Hydrogels can be delivered into the endoluminal wall. The hydrogels can be formed from hydrogel precursors that crosslink with each other in situ in the endoluminal wall. Described herein are various medical devices and methods, including injecting a hydrogel or liquid hydrogel precursors into the wall of an anatomical cavity (vessels or other hollow organs) to form a gel-based support matrix as an Extraluminal Scaffold or an Endomural Stent.

BRIEF DESCRIPTION OF THE DRAWINGS

FIG. 3A is a longitudinal cross-sectional view of an anatomical lumen that shows a liquid/gel delivery into a luminal wall;

FIG. 3B is a transverse cross-sectional view of the lumen of FIG. 3A taken along line BB;

FIG. 3C is a perspective view of the device used in FIG. 3A,

FIG. 4A is a longitudinal cross-sectional view of an anatomical lumen that shows a liquid/gel delivery into a luminal wall;

FIG. 4B is a transverse cross-sectional view of the lumen of FIG. 4A taken along line BB;

FIG. 4C is a perspective view of the device used in FIG. 4A,

DETAILED DESCRIPTION

Figure 1A:
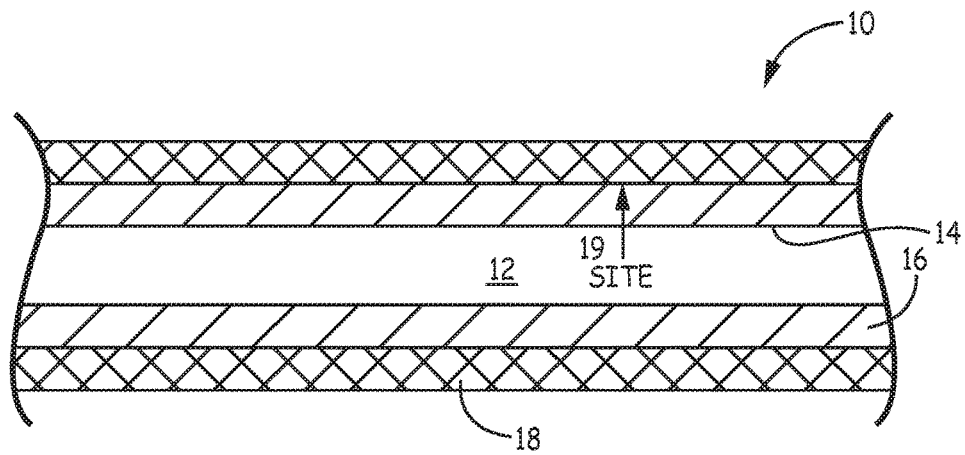
FIG. 1A is a longitudinal cross-sectional view of an anatomical lumen, and shows a site of introduction at an adventitia.

Described herein are a number of devices and methods of forming a hydrogel in a tissue, including natural or artificial potential spaces, a wall of an anatomical cavity (vessels or other hollow organs), and a wall of a blood vessel. The hydrogel may be used to provide a stenting action and/or to maintain patency of a body lumen. The hydrogel may hold a lumen of the vessel, organ, or space open without causing flow restrictions, unacceptable inflammation, undue disruption of the lumen or tearing of the tissue. Embodiments include, for instance, forming a gel-based support matrix as an extra-luminal scaffold or an endomural stent. The hydrogels may also be used to deliver a therapeutic agent (such as an active pharmaceutical ingredient (API)) at the luminal wall, media, adventitia, or surrounding tissues with the shortest path of diffusion from the suspension into the luminal wall and/or other surrounding tissues. Hydrogel formulations can be tailored using factors such as: persistence of the hydrogel after implantation by controlling a hydrolysis-driven degradation rate; crosslinking conditions to facilitate control of the hydrogel distribution and shape as it crosslinks in situ following injection; and mechanical properties of the crosslinked material, such as modulus, hydrophilicity, strength, and cohesiveness.

Suspending the agent in a hydrogel can allow the agent to persist and be bioavailable for a longer duration in the luminal wall than an aqueous solution or suspension. Longer persistence of therapeutic levels of the agent reduces the frequency that the agent needs to be readministered. A hydrogel reduces the agent washout that may occur with aqueous solutions and suspensions as well. Moreover, the agent can be disposed in various forms inside the hydrogel—in particles, in control-release particles (e.g., liposomes, micelles, capsules), as a solid, as an insoluble drug, and so forth. One such embodiment is to dispose the drug inside particles made of another hydrogel, with the various forms of the agent being options for disposition in one or both of the hydrogels. Further, a non-fluent hydrogel can help to seal at the site of its introduction.

One of the challenges in this field is that the hydrogel is preferably a uniform material with a shape suited for delivery of the agent. A uniform material provides for consistent and controllable results. A single cohesive mass of material creates a three-dimensional space having a geometry suited to certain kinds of controlled release of the agent. Certain kinds of controlled release schemes are enabled when a cohesive mass is created. Alternatively, merely scattering particles containing an agent a short distance from their site of introduction at the luminal wall or other space provides a different delivery condition. Placement of the hydrogel between the layers of the luminal wall presents enhanced opportunities for controlled release including rapid drug diffusion into the endomural space or sustained delivery of the drug(s) over time using a permanent or resorbable endomural stent structure. Placement of the hydrogel between the layers of the luminal wall also allows for a permanent endomural stent construction, a permanent endomural structure, or a resorbable endomural stent structure to mechanically prop the lumen open and maintain such opening. Precursors that are cohesive at the pre-crosslinking stage may be chosen, as well as precursors that form cross-links with each other.

Figure 1B:
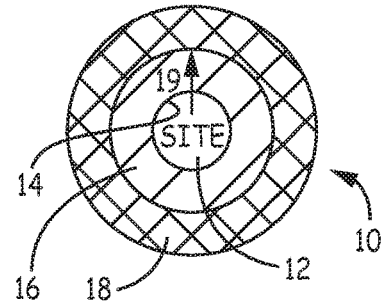
FIG. 1B is a transverse cross-sectional view of the lumen of FIG. 1A.
Figure 2A:
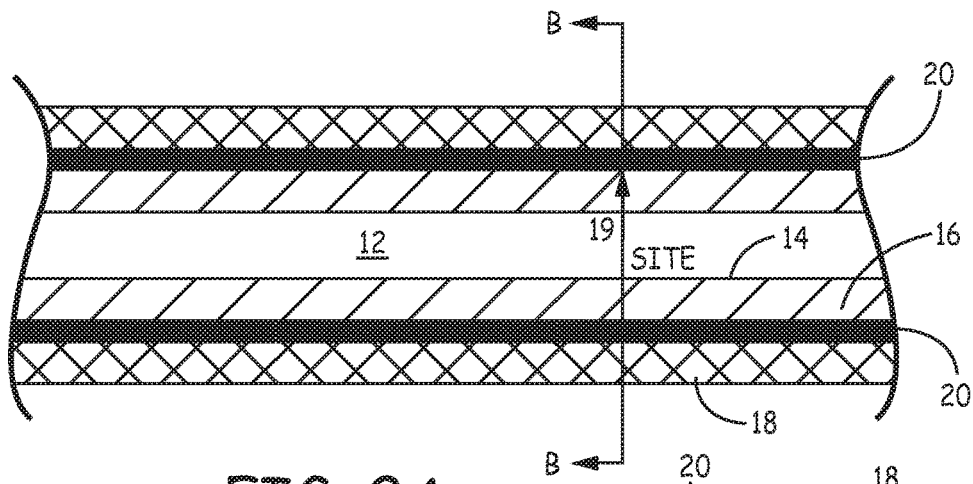
FIG. 2A depicts a hydrogel introduced at the site of FIG. 1, with an agent, at an adventitia.
Figure 2B:
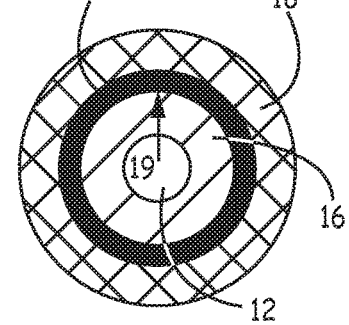
FIG. 2B is a transverse cross-sectional view of the lumen of FIG. 2A taken along line BB.

FIG. 1 depicts a site of injection in an anatomical lumen. By way of overview, blood vessel 10 has lumen 12 surrounded by a layer of endothelial cells 14 that is surrounded by media 16 that is surrounded by adventitia 18. A site 19 receives an injection or other introduction of a hydrogel or hydrogel precursors. The hydrogel or hydrogel precursors flow from the site (or sites) into the wall of the blood vessel. FIG. 2 shows cohesive hydrogel layer 20 at an adventitia-media location. Hydrogel precursors, drug loaded hydrogel particles, or drug-containing dried pastes may be injected into the luminal wall. These methods create an area of contact within the luminal wall. An area of contact could be, e.g., from 0.1 to 60 $mm^2$; artisans will immediately appreciate that all ranges and values within this range are contemplated and supported, e.g., 1, 2, 5, 6, or 8 $mm^2$. A height, considered independently or in addition to an area of contact may be, e.g., 10 µm to 5 mm.

In general, to form a hydrogel, one or more precursors are reacted. The precursors form crosslinks that prevent the dissolution of the hydrogel in water. Precursors may be crosslinked via an ionic or covalent bond, a physical force, or other attraction. A covalent crosslink, however, will typically offer stability and predictability in reactant product architecture. To form covalently crosslinked hydrogels, the precursors are covalently crosslinked together. In general, precursors are joined to other precursors at two or more points, with each point being a linkage to the same or different polymers. Precursors with at least two reactive centers (for example, in free radical polymerization) can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. These are described in some detail, below.

The precursors may be injected or otherwise introduced into a luminal wall area, where they will form a hydrogel. The precursors may be chosen to have a delayed time of crosslinking to provide for flow of the precursors in and around the site of initial introduction. The hydrogel may be prepared as a paste. The precursors of the hydrogel may be a paste and form crosslinks inside the wall. Or a hydrogel may be prepared as a collection of hydrogel particles that are prepared as a fluent paste. The paste of precursors and/or paste of hydrogel may be forced into the luminal wall. A paste is a viscous fluid that will flow only in response to a force applied to it. Moreover, the paste may be prepared as a gel that is not crosslinked before or after placement. For instance, the paste may comprise a gel comprising polymers, e.g., thermoresponsive polymers such as PLURONIC F127 gels or polysaccharide preparations, e.g., hyaluronic acid.

Devices

FIGS. 3-7 depict some embodiments of devices and methods for injecting materials at in a luminal wall or other location. Alternatively, conventional techniques for placement of a material at a luminal wall may be used.

FIG. 3 demonstrates medical balloon 30 with one or more holes 32 or other predetermined openings to build enough pressure during injection of fluent precursors, in order for the balloon to fill the target hollow luminal space, get approximated to the luminal wall, and drive the precursors with adequate hydraulics into the luminal wall, media, adventitia or surrounding tissues.

FIG. 4 demonstrates a balloon 40 lined with one or more flexible hollow tubes 42 with one or more holes 44 with predetermined openings. In this embodiment the balloon is inflated at a desired pressure to expand and fill the hollow intraluminal space and drive the delivery tube(s) 42 against the endoluminal wall. Next, the fluent precursors are injected independently through the delivery tubes endomurally into the luminal wall, media, adventitia or surrounding tissues.

Figure 5A:
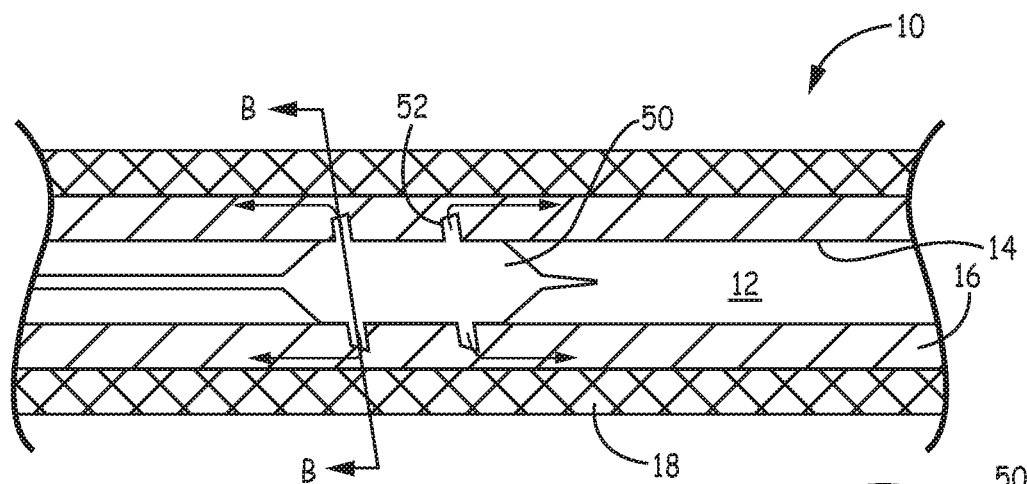
FIG. 5A is a longitudinal cross-sectional view of an anatomical lumen that shows a liquid/gel delivery into a luminal wall.
Figure 5B:
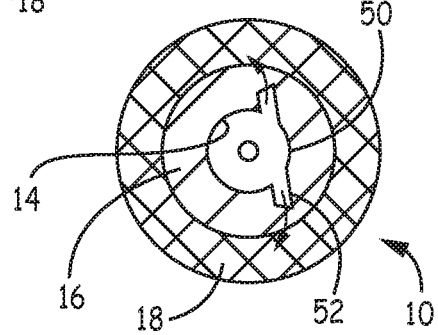
FIG. 5B is a transverse cross-sectional view of the lumen of FIG. 5A taken along line BB.

FIG. 5 demonstrates a balloon system 50 integrated with one or more needles 52 of predetermined size to build enough pressure during injection of the fluent precursors for balloon 50 to fill the target hollow luminal space, drive needle(s) 52 into the luminal wall, and drive the precursors with adequate hydraulics endomurally into the luminal wall, media, adventitia or surrounding tissues. Examples of micro needles can be found in U.S. Pat. No. 8,740,849 to Fischell et al., U.S. Pat. No. 8,465,752 to Seward, U.S. Pat. No. 8,721,590 to Seward et al., and U.S. Pat. No. 7,141,041 to Seward, which are hereby incorporated by reference herein in their entirety to the extent they do not contradict what is explicitly disclosed herein.

Figure 6A:
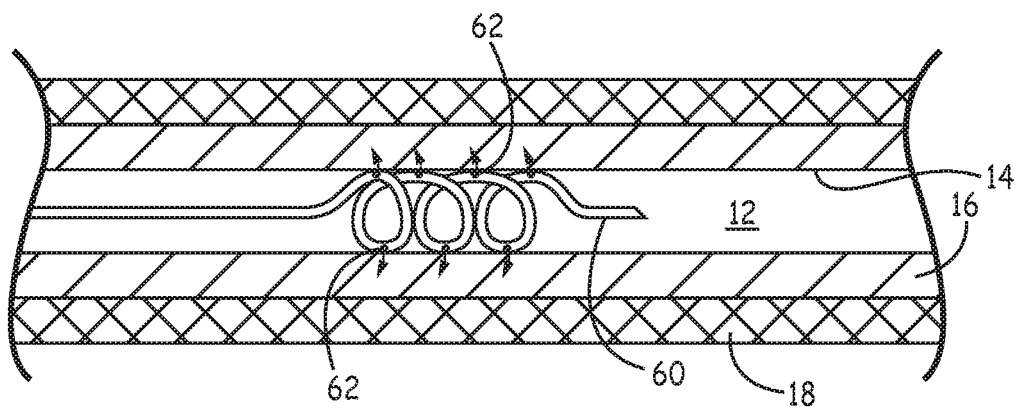
FIG. 6A is a cut-away view of an anatomical lumen that shows a liquid/gel delivery from a helical hypowall into a luminal wall.
Figure 6B:
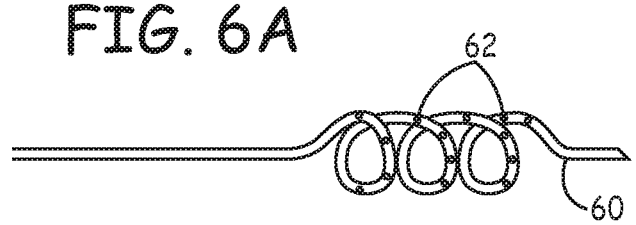
FIG. 6B is a perspective view of the device used in FIG. 6A.

FIG. 6 demonstrates a non-balloon-based system of hypotube(s) 60 which may be oriented in a helical fashion or in a weaved or woven style, to be mechanically expandable through some form of mechanical actuation. The actuation causes hypotube(s) 60 to expand in the targeted space, and certain holes/openings created in the expandable part of the hypotubes, whereby such expandable region is approximated to the luminal wall, and allow for the pre-polymers to be injected into the luminal wall, media, adventitia or surrounding tissues with adequate hydraulics. Holes 62 are forced against the walls of lumen 12 when tubes 6 are expanded.

Figure 7:
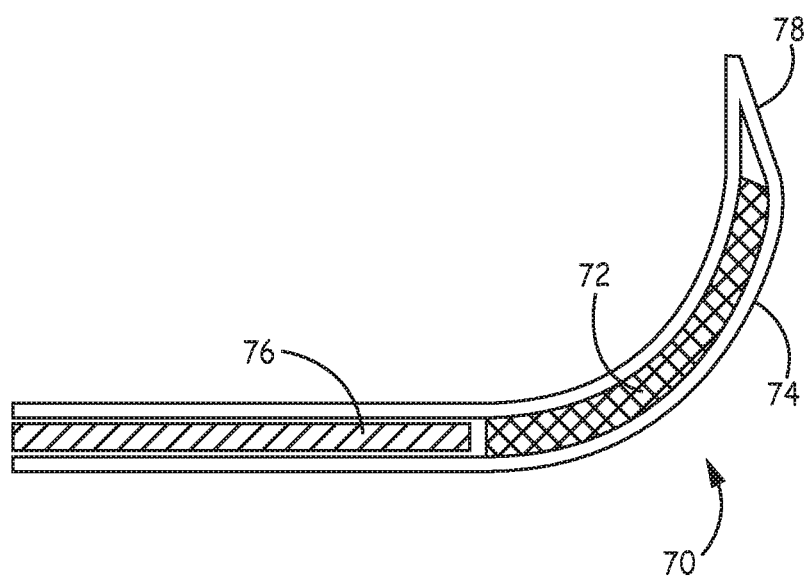
FIG. 7 is a partial cross sectional view of a device comprising a curved needle and a pushing mandrel for delivering an injectable paste into a luminal wall.

FIG. 7 demonstrates a needle system 70 for injecting an injectable paste 72. In this embodiment, a nitinol or other flexible needle 74 that bends as it is advanced from a sheath is inserted into the luminal wall. The needle 74 is preloaded with a drug containing dried paste 72, for example using a polyethylene glycol hydrogel base. A pushing mandrel 76 is then advanced once the needle is positioned, pushing the paste into the perivascular space. The mandrel tip 78 may be very flexible (for example, a spring), to avoid altering the shape of the needle as it is advanced.

Precursor Materials

The hydrogels are made from precursors. Precursors are chosen in consideration of the properties that are desired for the resultant hydrogel. There are various suitable precursors for use in making the hydrogels. The term precursor refers to those molecules crosslinked to form the hydrogel or organogel matrix. While other materials might be present in the hydrogel or organogel, such as therapeutic agents or fillers, they are not precursors. Hydrogels are materials that do not dissolve in water and retain a significant fraction (more than 20%) of water within their structure. In fact, water contents in excess of 90% are often known. Hydrogels may be formed by crosslinking water soluble molecules to form networks of essentially infinite molecular weight.

Hydrogels with high water contents are typically soft, pliable materials. Hydrogels and drug delivery systems as described in U.S. Publication Nos. 2009/0017097, 2011/0142936 and 2012/0071865 may be adapted for use with the materials and methods herein by following the guidance provided herein; these references are hereby incorporated herein by reference for all purposes, and in case of conflict, the instant specification is controlling.

Hydrogels may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratin sulfate, keratosulfate, and derivatives thereof. In general, the glycosaminoglycans are extracted from a natural source and purified and derivitized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum crosslinked with a polyol such as propylene glycol, and the like, also form hydrogels upon contact with aqueous surroundings.

Synthetic hydrogels may be biostable or biodegradable. Examples of biostable hydrophilic polymeric materials are poly(hydroxyalkyl methacrylate), poly(electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

Hydrogels may be made from precursors. The precursors are crosslinked with each other. Crosslinks can be formed by covalent bonds or physical bonds. Examples of physical bonds are ionic bonds, hydrophobic association of precursor molecule segments, and crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form matrices and/or polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein. Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule. Some precursors react by a step growth mechanism, and are polymers formed by the stepwise reaction between functional groups of monomers. Most step growth polymers are also classified as condensation polymers, but not all step growth polymers release condensates. Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons. The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al., U.S. Pat. Nos. 5,100,992 and 4,826,945 to Cohn et al., or U.S. Pat. Nos. 4,741,872 and 5,160,745 to DeLuca et al., each of which is hereby incorporated by reference herein in its entirety to the extent it does not contradict what is explicitly disclosed herein.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic molecule, e.g., a precursor or precursor portion, has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic. As is customary in these arts, the term PEG is used to refer to PEO with or without hydroxyl end groups.

A precursor may also be a macromolecule (or macromer), which is a molecule having a molecular weight in the range of a thousand to many millions. The hydrogel or organogel however, may be made with at least one of the precursors as a small molecule of about 1000 Da or less (alternatively: 2000 Da or less). The macromolecule, when reacted in combination with a small molecule (of about 1000 Da or less/200 Da or less), is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000. There are certain advantage to having a small molecule, such as diffusivity for completion of reactions.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivitized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, PLURONIC F 127, JEFFAMINE, or TETRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in U.S. Publication Nos. 2004/0086479 and 2004/0131582 and PCT Publication Nos. WO2007005249, WO2007001926 and WO2006031358, or the U.S. counterparts thereof; dendrimers may also be useful as multifunctional precursors, e.g., as in U.S. Publication Nos. 2004/0131582 and 2004/0086479 and PCT Publication No. WO2006031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivitized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight). Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivitized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. NH2 refers to an amine termination. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable or water-degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels, as well as compositions that comprise the same, may be provided in a form that is pharmaceutically acceptable, meaning that it is highly purified and free of contaminants, e.g., pyrogens.

Hydrogel Structures

The hydrogel's structure and the material composition of the hydrogel's precursors determine its properties. Precursor factors include properties such as biocompatibility, water solubility, hydrophilicity, molecular weight, arm length, number of arms, functional groups, distance between cross-links, degradability, and the like. The choice of reaction conditions also effects the hydrogel's structure and properties, including choices of solvents, reaction schemes, reactant concentrations, solids content, and the like. There can be a variety of ways to achieve certain properties, or combination of properties. On the other hand some properties are in tension with each other, for instance brittleness may increase as a distance between crosslinks decreases or solids content increases. Strength may be increased by increasing the number of crosslinks but swelling may thereby be reduced. Artisans will appreciate that the same materials may be used to make matrices with a great range of structures that will have highly distinct mechanical properties and performance, such that the achievement of a particular property should not be merely assumed based on the general types of precursors that are involved.

The spacing between molecular strands of the hydrogel (the matrix) affects several hydrogel properties, including a rate of diffusion of molecules. The crosslinking density can be controlled by the choice of the overall molecular weight of the precursor(s) used as crosslinker(s) and other precursor(s) and the number of functional groups available per precursor molecule. A lower molecular weight between crosslinks such as 200 will give much higher crosslinking density as compared to a higher molecular weight between crosslinks such as 500,000; artisans will immediately appreciate that all ranges and values within this range are contemplated and supported, e.g., 200 to 250,000, 500 to 400,000, and so forth. The crosslinking density also may be controlled by the overall percent solids of the crosslinker and functional polymer solutions. Yet another method to control crosslink density is by adjusting the stoichiometry of nucleophilic functional groups to electrophilic functional groups. A one to one ratio leads to the highest crosslink density. Precursors with longer distances between crosslinkable sites form gels that are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 1,000 to 100,000; artisans will immediately appreciate that all the ranges and values within the explicitly stated ranges are contemplated, e.g. 5,000 to 35,000. The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%.

In some embodiments, lower molecular weight precursors allow for fairly stiff mechanical stenting of the luminal wall using a hydrogel. Because the hydrogel is embedded in the luminal wall, it is less likely to fragment. A person of ordinary skill in the art will recognize that additional ranges are contemplated and are within the present disclosure.

In some embodiments, the precursors may be able to be diluted prior to reacting. This allows any residue left with in the lumen to be diluted downstream.

In some embodiments, the hydrogel is designed to gel in between about 1 minute and about 10 minutes. In further embodiments the hydrogel is designed to gel in between about 1 minute and about 5 minutes, or in between about 1 minute and about 3 minutes. A person of ordinary skill in the art will recognize that additional ranges are contemplated and are within the present disclosure.

Functional Groups

The precursors for covalent crosslinking have functional groups that react with each other to form the material via covalent bonds, either outside a patient, or in situ. The functional groups generally are polymerizable, a broad category that encompasses free radical, addition, and condensation polymerization and also groups for electrophile-nucleophile reactions. Various aspects of polymerization reactions are discussed in the precursors section herein.

Thus in some embodiments, precursors have a polymerizable group that is activated by photoinitiation or redox systems as used in the polymerization arts, or electrophilic functional groups, for instance: carbodiimidazole, sulfonyl chloride, chlorocarbonates, n-hydroxysuccinimidyl ester, succinimidyl ester or sulfasuccinimidyl esters, or as in U.S. Pat. No. 5,410,016 or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di-or multifunctional poly(ethylene glycol) can be used.

One embodiment has reactive precursor species with 2 to 16 nucleophilic functional groups each and reactive precursor species with 2 to 16 electrophilic functional groups each; artisans will immediately appreciate that all the ranges and values within the explicitly stated ranges are contemplated, for instance 2, 3, 4, 5, 6, 7, 8, 9, 10, 11, 12, 13, 14, 15, or 16 groups.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2, 2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Visualization Agents

A visualization agent may be used as a powder in a xerogel/hydrogel; it reflects or emits light at a wavelength detectable to a human eye so that a user applying the hydrogel could observe the object when it contains an effective amount of the agent. Agents that require a machine aid for imaging are referred to as imaging agents herein, and examples include: radioopaque contrast agents and ultrasound contrast agents. Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. Visualization agents may be covalently linked to the molecular network of the xerogel/hydrogel, thus preserving visualization after application to a patient until the hydrogel hydrolyzes to dissolution. Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. Reactive visualization agents such as NHS-fluorescein can be used to incorporate the visualization agent into the molecular network of the xerogel/hydrogel. The visualization agent may be present with either reactive precursor species, e.g., a crosslinker or functional polymer solution. The preferred colored substance may or may not become chemically bound to the hydrogel.

Biodegradation

A hydrogel may be formed so that, upon hydration in physiological solution, a hydrogel is formed that is water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids. The term degradation by solvation in water, also referred to as dissolving in water, refers to a process of a matrix gradually going into solution in, which is a process that cannot take place for a covalently crosslinked material and materials insoluble in water.

For example, electrophilic groups such as SG (N-hydroxysuccinimidyl glutarate), SS (N-hydroxysuccinimidyl succinate), SC (N-hydroxysuccinimidyl carbonate), SAP (N-hydroxysuccinimidyl adipate) or SAZ (N-hydroxysuccinimidyl azelate) may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment. Some embodiments include precursors that are free of adjacent ester groups and/or have no more than one ester group per arm on one or more of the precursors: control of the number and position of the esters can assist in uniform degradation of the hydrogel.

A biodegradable linkage in the organogel and/or xerogel and/or hydrogel and/or precursor may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly (carbonate)s, and poly(phosphonate)s.

If it is desired that a biocompatible crosslinked matrix be biodegradable or absorbable, one or more precursors having biodegradable linkages (or just one biodegradable linkage, for example an ester) present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Hydrogel Loading with Agents; Preparation as Particles

One approach for making a hydrogel or organogel with a therapeutic agent is to form it around the agent. For instance, a first precursor is added to a solvent-protein mixture, followed by a second precursor that is reactive with the first precursor to form crosslinks. After formation of the matrix in the solvent, the solvent may be removed to form a xerogel. Potential processes include, e.g., precipitation with non-solvent, nitrogen sweep drying, vacuum drying, freeze-drying, a combination of heat and vacuum, and lyophilization. If molten precursors are used in the absence of a tertiary solvent, there is no need to employ any solvent removal process. Upon cooling the material forms a rubbery solid (if above Tm), a semirigid semicrystalline material (if below Tm) or a rigid glassy solid (if below Tg). These materials are more dense than xerogels formed from organic solvents. When filled with particles of other materials, e.g., therapeutic agents, buffer salts, visualization agents, they can be highly porous, since the solid particles create and fill the pores.

In some embodiments, the agent or agents are present in a separate phase when precursors are reacted. The separate phase could be oil (oil-in water emulsion), or an immiscible solvent, a liposome, a micelle, a biodegradable vehicle, and the like. Biodegradable vehicles in which the active agent may be present include: encapsulation vehicles, such as microparticles, microspheres, microbeads, micropellets, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly (orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone) s and poly (hydroxy acid) are particularly preferred as biodegradable encapsulation vehicles. The therapeutic agent or encapsulated therapeutic agent may be present in solution or suspended form. Some agents are highly soluble while others are effectively insoluble in aqueous solution and can form their own phase when exposed to aqueous solvent.

Therapeutic agents can be in solid particulate form in the hydrogel, e.g., as a powder. For instance, water soluble biologics (e.g., proteins) in solid phase can be ground or otherwise formed into a fine powder that is added to the precursors when a matrix is formed. The peptide or other water soluble biologic may be in a solid phase, may be all crystalline, partially crystalline, or essentially free of crystals (meaning more than 90% free of crystals w/w; artisans will immediately appreciate that all the ranges and values within the explicitly stated ranges are contemplated). A powder of a protein refers to a powder made from one or more proteins. Similarly, powders of water soluble biologics are powders having particles made of one or more water soluble biologics. The powders and/or xerogels and/or organogels and/or hydrogels that contain them may be free of encapsulating materials and be free of one or more of a liposome, micelle, or nanocapsule. Further, a protein particle or a water soluble biologic particle may be made that is free of one or more of: binders, non-peptidic polymers, surfactants, oils, fats, waxes, hydrophobic polymers, polymers comprising alkyl chains longer than 4 $CH_2$ groups, phospholipids, micelle-forming polymers, micelle-forming compositions, amphiphiles, polysaccharides, polysaccharides of three or more sugars, fatty acids, and lipids. Lyophilized, spray dried or otherwise processed proteins are often formulated with sugars such as trehalose to stabilize the protein through the lyophilization or other processes used to prepare the proteins. These sugars may be allowed to persist in the particle throughout the organogel/xerogel process. The particles may be made to comprise between about 20% and about 100% (dry w/w) protein; artisans will immediately appreciate that all the ranges and values within the explicitly stated ranges are contemplated, e.g., about 50% to about 80% or at least 90% or at least about 99%. A number of factors can be controlled that contribute to processing and delivery of a protein without denaturation. The protein may be prepared as a powder, with the powder particle size being chosen in light of the size of the ultimate hydrogel/organogel/xerogel particle. Organic solvents for the proteins may be chosen so that the proteins are not solvated by the organic solvents and are compatible with the protein. Another factor is oxygen, and elimination of oxygen is helpful in processing to avoid denaturation. Another factor is chemical reactions. These may be avoided by keeping the protein in a solid phase and free of solvents that dissolve the protein until such time as the protein is implanted.

An organogel or hydrogel may be formed and then reduced to particles that are subsequently treated to remove the organic or aqueous solvent or solvents to form a xerogel. For an injectable form, the organogel or hydrogel can be macerated, homogenized, extruded, screened, chopped, diced, or otherwise reduced to a particulate form. Alternatively, the organogel or hydrogel can be formed as a droplet or a molded article containing the suspended protein particles. One process for making such particles involves creation of a material that is broken up to make the particles. One technique involves preparing the organogel or hydrogel with protein particles and grinding it, e.g., in a ball mill or with a mortar and pestle. The matrix may be chopped or diced with knives or wires. Or the matrix may be cut-up in a blender or homogenizer. Another process involves forcing the organogel through a mesh, collecting the fragments, and passing them through the same mesh or another mesh until a desired size is reached.

The particles of biologics or the particles or organogels or the particles of the xerogels may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated, e.g., from about 1 to about 10 µm or from about 1 to about 30 µm. About 1 to about 500 microns is another such range that is useful, with sizes falling throughout the range and having a mean sizing at one value within the range, and a standard deviation centered around the mean value, e.g., from about 1% to about 100%. A simple method for sizing particles involves using custom-made or standardized sieve mesh sizes. The term particle is broad and includes spheres, discs, and irregularly shaped particles. A spheroidal particle refers to a particle wherein the longest central axis (a straight line passing through the particle's geometric center) is no more than about twice the length of other central axes, with the particle being a literally spherical or having an irregular shape. A rod-shaped particle refers to a particle with a longitudinal central axis more than about twice the length of the shortest central axis. Embodiments include making a plurality of collections of particles, with the collections having different rates of degradation in vivo, and mixing collections to make a biomaterial having a degradation performance as desired.

Pastes may be prepared that comprise the particles. The particles are prepared with a liquid, typically an aqueous, pharmaceutically acceptable liquid. The particles can be added to aqueous solution and then the water can be removed by filtering, vacuum, freeze drying, and/or gentle heat. The particles can be quickly removed from the solution, or may be allowed to hydrate or partially hydrate before processing them to form a paste.

The Lumen

Administration of a hydrogel may be performed directly into the site of interest. Embodiments of the invention include administration in or near a luminal wall. An anatomical lumen is an inner open space or cavity of an organ. For example, a blood vessel, ureter, esophagus, bile duct, or an intestine has a lumen. The lumen may be permanent, e.g., a blood vessel, or potential, e.g., Denonvilliers space. The structure of a blood vessel, for example, can be divided into three main layers or tunics: the tunica intima, the tunica media, and the tunica adventitia. The tunica intima is the innermost layer of the vessel wall. It is a thin layer of endothelial cells which lines the circulator system. The tunica media is the muscular middle layer of arteries and veins. It contains the smooth muscle, as well as elastic fiber and connective tissue. The tunica adventitia is made entirely of connective tissue and contains the nerves that supply the vessels. Other body lumens may also benefit from stenting including, for example, the urethra. The luminal walls of other lumens contain other layers and structures. These layers are referred to in this application generally as the endoluminal wall, referring to the innermost layer, and the outer wall, referring to the outermost layer.

In use, for example a balloon catheter or other device is used to deliver precursors. When precursors are delivered, they are chosen so they form hydrogel in situ. The term in situ refers to forming the device, hydrogel, or gel at the site of intended use; for implanted materials, the site of intend use is the location of the implant, i.e., in the body. The therapeutic agents are released from the hydrogels. Various sites may be chosen. Sites where drug delivery depots or stents may be formed include the luminal wall, media, adventitia, endoluminal wall, outer luminal wall, or surrounding tissues.

Placement

The delivery devices may be used to deliver their contents to any site, including any soft or hard tissue, and placement, e.g., intramuscular, intraperitoneal, subcutaneous. Their contents may be a precursor or agent as set forth herein, or other materials.

The hydrogel may be placed at a site that is suited to deliver the agent for the pathology that is being treated. The choice of dose, size of implant, and position is affected by factors such as a time between repeat administrations, patient comfort or compliance, and dosage received at a target tissue.

The hydrogel may be placed so that the hydrogel is free of contact with fluids carried by the lumen. Accordingly, the hydrogel is entirely within the tissue where it is placed and free of contact with fluids excepting fluids in, or of, the tissue. In the case of a luminal wall, the hydrogel is entirely within the wall. This placement gives the advantage of not having sequelae and of not having hydrogel components or degradation products compromise the luminal patency over time. This placement also offers the advantage of better retention of the hydrogel where it is administered, and thus prevents migration over time. This placement is distinct from other approaches that place a hydrogel material directly on the wall of a lumen, e.g., photopolymerizing gels.

Embodiments include placement of a bioabsorbable stent at a locus of, for example, a blood vessel, e.g., a vein, an artery, a femoral vein, a leg vein, a deep leg vein, a peripheral vein, a peripheral artery, a coronary artery and/or a stenotic portion thereof. The stent assists in maintaining patency and may further comprise agents for delivery to the site.

In some embodiments, an angioplasty or similar procedure is preformed to dilate the lumen. A hydrogel or hydrogel precursor is injected into the luminal wall. The hydrogel is then allowed to set for at least about 1 minute, at least about 2 minutes, at least about 5, or at least about 10 minutes. A person of ordinary skill in the art will recognize that additional ranges are contemplated and are within the present disclosure. Expansion of the stent to its final configuration can thus be augmented and/or facilitated by, for example, inflating a balloon catheter in the lumen to expand the walls and provide for the stent to have a maximal diameter and to preserve as much patency as possible. Moreover, the site can be treated before, during or after dilation of the lumen, for instance arterial plaque can be compressed at the time of stent placement, before placement, or in addition to placement.

A stent and/or drug depot of the in-situ hydrogel drug delivery implant may be designed for controlled, long term drug release ranging from, e.g., about one to about three months, or longer, depending on the site, dose, and so forth, e.g., 1-12 months.

Conditions and sites for placement of stents and/or hydrogels include luminal walls for: stenosis or restenosis of veins, arteries, or a vascular structure; for urethral stenosis of benign prostate hyperplasia or a (benign or malignant) stricture of an esophagus; and for bile duct occlusions. A bowel lumen may be stented with a hydrogel in a bowel wall, for instance, in inflammatory bowel disease and Crohn's disease there are segments within the bowel that are ulcerated and need treatment.

Placement of hydrogels in a tissue or a wall of a lumen can provide stenting where conventional stents are not useful. For instance, conventional stents have a stiffness that limits the distance and the tolerable amount of tortuosity involved in threading them through a vasculature to a site of use. Moreover, some conditions require lengthy stenting or multiple stents that are more difficult to place, for instance long segments of artery in peripheral artery disease.

The stents or hydrogels can carry a drug payload of various types of therapeutic agents for various conditions, of which some include, for example, steroids, antibiotics, NSAIDS, stabilizing agents and/or antiangiogenic agents, or combinations thereof. The in-situ implant embodiments can improve the efficacy and pharmacokinetics of potent therapeutic agents in the treatment of chronic vascular diseases and minimize patient side effects in several ways. First, the implant can be placed in vessel at a specific disease site, bypassing the topical or systemic routes and thereby increasing drug bioavailability. Secondly, the implant maintains local therapeutic concentrations at the specific target tissue site over an extended period of time.

A hydrogel is formed in situ. In some embodiments the hydrogel is comprised of at least 50%, 75%, 80%, 90%, or 99% w/w water-soluble precursors (calculated by measuring the weight of the hydrophilic precursors and dividing by the weight of all precursors, so that the weight of water or solvents or non-hydrogel components is ignored) to enhance the non-adhesive properties of the hydrogel. In some embodiments, such hydrophilic precursors substantially comprise polyethylene oxides. In some embodiments, drugs to reduce tissue adherence mediated by biological mechanisms including cell mitosis, cell migration, or macrophage migration or activation, are included, e.g., anti-inflammatories, anti-mitotics, antibiotics, PACLITAXEL, MITOMYCIN, or taxols.

In some embodiments, the tunica intima may be punctured or penetrated with a needle or catheter or trocar and precursors introduced into a space between the intima and the media, the media and the adventitia, or other spaces in the luminal wall. In some cases the intima may be punctured to access a natural potential space between the tissues that is filled by the precursors. In other cases, a potential or actual space is created mechanically with a trocar, spreader, or the like, that breaks the adherence between the sclera and conjunctiva so that precursors may be introduced. The vessel wall has enough elasticity to allow useful amounts of precursors to be introduced or forced into such natural or created spaces.

In some aspects, in-situ formation of the hydrogel lets the hydrogel gel or crosslink in place, so that it does not flow back out through the tract of the needle and diffuse into the lumen through the incision site upon the removal of the needle or cannula. A shape-stable hydrogel thus formed can effectively deliver the drug and advantageously can have well-controlled size, shape, and surface area. A small needle may be used to inject the materials since soluble or flowable precursors may be used instead of an already-formed material. By way of contrast, alternative materials that do not cross-link quickly and firmly upon introduction tend to flow back out of the incision. And materials that do not covalently cross-link are subject to creep or weeping as the material continually reorganizes and some or all of the material flows out.

Materials set forth herein, e.g., precursors, hydrogels, or gels, may be placed outside of a tissue, or may be formed anywhere outside of the lumen. In the vasculature, for instance, placement may be the media, adventitia, and the loose connective tissue blood vessels. Accordingly, delivery may be intravascular, or intraluminal in the case of non-vascular lumens, and the material is delivered outside of the wall of the lumen. Such materials may be for stenting, if appropriately positioned, and/or for delivery of a therapeutic agent.

Kits

Kits or systems for making hydrogels may be prepared so that the precursor(s) and therapeutic agent(s) are stored in the kit with diluents as may be needed. Applicators may be used in combination with the same. The kits are manufactured using medically acceptable conditions and contain components that have sterility, purity and preparation that is pharmaceutically acceptable. Solvents/solutions may be provided in the kit or separately, or the components may be pre-mixed with the solvent. The kit may include syringes and/or needles for mixing and/or delivery. The kit or system may comprise components set forth herein.

Administration

An embodiment is a hydrogel formed by in situ polymerization containing a therapeutic agent. In use, precursors and the agent(s) and injected into the site of intended use in the patient. The precursors react with each other to form the hydrogel. A needle, cannula, trocar, sprayer, or other applicator may be used. Administration of the hydrogels and/or xerogels may also involve hydration in advance, at about the time of use, or at the point of use.

The materials described herein may be used to deliver drugs or other therapeutic agents (e.g., imaging agents or markers). One mode of application is to apply a mixture of precursors and other materials (e.g., therapeutic agent, buffer, accelerator, initiator) through a needle, microneedle, cannula, catheter, or hollow wire to a site. The mixture may be delivered, for instance, with a device as set forth herein, with a manually controlled syringe, or with mechanically controlled syringe, e.g., a syringe pump. Alternatively, a dual syringe or multiple-barreled syringe or multi-lumen system may be used to mix the materials at or near the site with a hydrating fluid and/or other agents. Balloon catheters with microneedles or one or more holes or minimally invasive injectors may be used to introduce the hydrogel into the luminal wall, see U.S. Pat. Nos. 8,975,233, 8,771,252, 8,465,752, and US 2014/0303569.

The precursors, gels, hydrogels, pastes, fluids, or other materials described herein may be injected with a needleless injection device, see U.S. Pat. Nos. 8,945,045, 8,876,759, and US 2011/0270216.

EXAMPLES

Example 1

Preparation and Injection of Hydrogels into a Luminal Tissue

A hydrogel or hydrogel precursors may be prepared and injected into luminal tissue using the following method. Trilysine Acetate is dissolved in a Sodium Phosphate Dibasic solution. NHS-Fluorescein (5(6)-Carboxyfluorescein, Succinimidyl Ester) (NHS-Fluorescein) is weighted and transferred to the vial containing the Trilysine Acetate/Sodium Phosphate Dibasic solution and vortexed until completely dissolved. The vial is immediately wrapped in foil to prevent light exposure and allowed to react for 1 hour.

After 1 hour, the Trilysine Acetate/NHS-Fluorescein/Sodium Phosphate Dibasic solution is aliquotted into a 5 mL syringe.

In a second 5 mL syringe, Dexamethasone, Micronized, USP is weighed. DI water is added to the syringe. The syringe plunger is then replaced and the syringe was vortexed to suspend the Dexamethasone.

Polyethylene glycol (PEG) end capped with succinimidylsuccinate groups (4a20kSG PEG) powder is transferred into a third 5 mL syringe, and mixed with a Sodium Phosphate Monobasic solution to dissolve the PEG.

The contents of the PEG/Sodium Phosphate Monobasic solution syringe and the Dexamethasone suspension syringe is combined by mating the two syringes with a luer-luer connector and passing the contents back and forth between the two syringes for approximately 10 seconds. The resulting mixture is then drawn into one syringe. The combined mixture created in the preceding step is then mixed with the Trilysine/NHS-Fluorescein/Sodium Phosphate Dibasic solution syringe using the same mixing method. This final mixing step initiates the crosslinking reaction, and a stopwatch is started at the onset of this final mixing step.

The hydrogel precursor solution is introduced into each of three Hamilton Glass Syringes. Each is then expelled through a microneedle of approximately 600 μm length and varying in inner diameter from 120 μm to 160 μm. The contents of each syringe are expelled freely and completely without visible signs of the micronized suspension remaining in the syringe or otherwise being obstructed by the small diameter of the needle.

Therapeutic agents for use may include, for instance, steroids, non-steroidal anti-inflammatory drugs (NSAIDS), anti-cancer drugs, antibiotics, an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). Therapeutic agents include classes of drugs including steroids, NSAIDS, antibiotics, pain relievers, inhibitors of vascular endothelial growth factor (VEGF), chemotherapeutics, anti-viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, peptides, proteins, RNA fragments, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

Therapeutic agents may include a protein or other water soluble biologics. These include peptides and proteins. The term protein, as used herein, refers to peptides of at least about 5000 Daltons. The term peptide, as used herein, refers to peptides of any size. The term oligopeptide refers to peptides having a mass of up to about 5000 Daltons. Peptides include therapeutic proteins and peptides, antibodies, antibody fragments, short chain variable fragments (scFv), growth factors, angiogenic factors, and insulin. Other water soluble biologics are carbohydrates, polysaccharides, nucleic acids, antisense nucleic acids, RNA, DNA, small interfering RNA (siRNA), and aptamers.

Further embodiments of therapeutic agents for delivery include those that specifically bind a target peptide in vivo to prevent the interaction of the target peptide with its natural receptor or other ligands. AVASTIN, for instance, contains bevacizumab, an antibody that binds VEGF. And AFLIBERCEPT is a fusion protein that includes portions of a VEGF receptor to trap VEGF. An IL-1 trap that makes use of the extracellular domains of IL-1 receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

FURTHER DISCLOSURE

All patents, patent applications, and publications referenced herein are hereby incorporated by reference herein in their entirety; in case of conflict, the specification is controlling. The following numbered statements are part of the specification.

1a. A method of treating a patient comprising forming, in situ, a covalently-crosslinked hydrogel in a luminal wall of the anatomical lumen. 1b. Alternatively, a method of treating a patient comprising forming, in situ, a hydrogel outside of a wall of a lumen, either on the interior luminal side, or on the exterior face of the wall. 1c. Alternatively, a method of forming a gel or a hydrogel in luminal wall of an anatomical lumen or on an interior wall of an anatomical lumen, or on an exterior of an anatomical lumen. 1d. Alternatively, a method of forming a hydrogel or a gel comprising placing an applicator inside an anatomical lumen and applying the gel or hydrogel to the interior wall of the lumen, inside the wall of the lumen, on the exterior wall of the lumen, or exterior to the lumen. 2. The method of 1 (meaning 1a, or 1b etc) being a method of treating a luminal pathology of the patient. 3. The method of 1 or 2 with the hydrogel providing a stent. 4. The method of any of 1-3 wherein the hydrogel is free of contact with the lumen, is free of contact with a contents of the lumen, is free of contact with fluids in the lumen, is contained entirely within the luminal wall, or is contained entirely within a tissue of the patient without contact with fluids exterior to the tissue. 5. The method of any of 1-4 wherein the hydrogel is used to treat a pathology of the luminal wall, to strengthen the wall, or to serve as a depot to release therapeutic agents that act in the wall, that act in the tissue, or that act at a site remote from the hydrogel. 6. The method of any of 1-5 wherein the hydrogel comprises a therapeutic agent that is released from the hydrogel. 7. The method of any of 1-6 comprising introducing a hydrogel precursor in aqueous solution at a(n injection) site in the luminal wall that flows from the site and reacts to form the hydrogel. Alternatively, the method of any of 1-6 comprising introducing a paste at a site in the luminal wall, with the paste comprising a gel or a hydrogel. 8. The method of 7 wherein the precursor is a first precursor, further comprising a second precursor in the aqueous solution, with the first precursor and second precursor crosslinking with each other to form the hydrogel. 9. The method of 7 wherein the solution or the paste has a first pH when introduced at the luminal wall and a second pH after the introduction, with the precursor being reactive at the second pH. 10. The method of 7 further comprising an initiator chemical in the (aqueous) solution, with the initiator initiating reaction of the precursor to form the hydrogel. 11. The method of any of 1-10 wherein the paste, the hydrogel or the gel, at the time of completing placement of the same at an intended site, has a height from about 0.1 mm to about 2 mm. Artisans will immediately appreciate that all ranges and values between the explicitly stated bounds are contemplated, with, e.g., any of the following being available as an upper or lower limit: 0.1, 0.2, 0.5, 1, 1.5, 1.9, 2. 12. The method of any of 1-11 wherein the paste, the hydrogel or the gel, at the time of completing placement of the same at an intended site, has a surface area sized from about 1 to about 150 mm$^2$. Artisans will immediately appreciate that all ranges and values between the explicitly stated bounds are contemplated, with, e.g., any of the following being available as an upper or lower limit: 1, 2, 3, 4, 5, 10, 20, 25, 30, 40, 50, 60, 80, 100, 125, 150. 13. The method of any of 1-12 wherein the paste, the hydrogel or the gel, at the time of completing placement of the same at an intended site, has a height from about 0.1 mm to about 2 mm and/or an area from about 10 to about 60 mm$^2$. Artisans will immediately appreciate that all ranges and values between the explicitly stated bounds are contemplated, with, e.g., any of the following being available as an upper or lower limit: 10, 12, 15, 20, 30, 40, 50, 55, 60. 14. The method of any of 1-13 wherein the gel, the paste, or the hydrogel, at the time of completing placement at the intended site, has a volume of between about 1 μl and about 5 ml. Artisans will immediately appreciate that all ranges and values between the explicitly stated bounds are contemplated, with, e.g., any of the following being available as an upper or lower limit: 1, 5, 10, 100, 1000 microliters, 1.5, 2, 2.5, 3, 4, 5, ml.

15. The method of any of 1-14 wherein the paste, the hydrogel or the gel, at the time of completing placement of the same at an intended site, further comprises a plurality of particles that comprise the therapeutic agent. 17. The method of 15 further comprising an additional amount of the same or a different therapeutic agent that is not in the particles and is in the gel, paste, or hydrogel. 18. The method of 15 wherein the particles are hydrogels that comprise the agent, which is in a solution, is a solid, or is in suspension. 19. The method of 15 wherein the particles are solid and comprise the agent. 20. The method of any of 1-19 comprising the therapeutic agent as a suspension in an aqueous phase of the hydrogel. 21. The method of 1 wherein the hydrogel is low-swelling, as measurable by the hydrogel having a weight increasing no more than about 50% upon exposure to a physiological solution for twenty-four hours relative to a weight of the hydrogel at the time of formation. 22. The method of any of 1-21 wherein the gel, paste, or hydrogel is water-degradable, as measurable by the hydrogel being dissolvable in vitro in an excess of water by degradation of water-degradable groups. 23. The method of 22 wherein the water-degradable groups are esters. 24. The method of any of 1-23 comprising the hydrogel, wherein the hydrogel is formed by combining a first synthetic precursor comprising nucleophilic groups with a second synthetic precursor comprising electrophilic groups to form covalent crosslinks by reaction of the nucleophilic groups with the electrophilic groups to form the hydrogel. 25. The method of 24 wherein the precursor is water soluble. 26. The method of 25 wherein the hydrogel is formed by combining a first synthetic precursor with a second synthetic precursor. 27. The method of any of 1-26 with the gel, hydrogel, paste, or particles or other delivery agents therein comprising a therapeutic agent, wherein the therapeutic agent is selected from the group consisting of dexamethasone, nifedipine, a steroid, an inhibitor of vascular endothelial growth factor, an antiangiogenesis agent, a small molecule drug, a protein, a nucleic acid, and a growth factor. 28. The method of any of 1-27 with comprising a therapeutic agent, wherein the therapeutic agent is released over a period of time that is at least about three days. 29. The method of any of 1-28 wherein a point at which cumulative 80% w/w of the therapeutic agent has been released is reached at a time between about 14 days and 9 months. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, weeks, 1, 2, 3, 4, 5, 6, 7, 8, 9 months. 30. The method of any of 1-29 wherein the gel, hydrogel, or paste is applied at a blood vessel, a vein, an artery, a femoral vein, a leg vein, a deep leg vein, a peripheral vein, a peripheral artery, or a coronary artery. The site may be, e.g., a stenotic site thereof. 31. The method of 30 further comprising puncturing an intima to access the media or the adventitia. 32. The method of any of 1-31 wherein the hydrogel is formed by combining a first precursor with a second precursor and allowing it to gel for at least about 1 minute. 33. The method of any of 1-31 wherein a site of application is in, on, or near a wall, wherein the wall has a pathology, the pathology being, e.g, a plaque, a weakness, an aneurysm, a disease, or a stenosis. 34. The method of 30 or 31 further comprising puncturing an endothelial wall. 35. The method of any of 1-34 wherein the wall, e.g., an endothelial wall, is punctured using a microneedle, hydraulics, or a combination thereof. 36. The method of any of 1-35 comprising administering the gel, paste, hydrogel, or precursor with a minimally invasive applicator comprising a needleless injector, a microneedle, or ports positioned in contact with a wall of a lumen. 37. The method of 36 wherein the needleless injector comprises a high pressure injector for moving the gel, paste, hydrogel, or precursor out of the applicator at high pressure and/or high velocity. 38. The method of 36 or 37 wherein the applicator comprises a balloon with microneedles and/or ports, e.g., comprising positioning a balloon catheter in contact with the luminal wall at a therapeutic site. 39. The method of any of 1-38 wherein the luminal wall is that of a blood vessel, ureter, vein, artery, aorta, bile duct, ureter, intestine, part of a gastrointestinal tract, esophagus, lymph duct, an aneurysm, a brain aneurysm, an abdominal aortic aneurysm, or a cardiac blood vessel, or a peripheral blood vessel. Ureter, blood vessel, vein, artery, aorta, an aneurysm, a brain aneurysm, an abdominal aortic aneurysm, or a cardiac blood vessel. 40. The method of any of 1-38 comprising placement of the gel, hydrogel, paste, or precursor for stenosis or restenosis of veins, arteries, or a vascular structure; for urethral stenosis of benign prostate hyperplasia or a (benign or malignant) stricture of an esophagus; or for a bile duct occlusion. 41. The method of any of 1-38 comprising placement of the gel, hydrogel, paste, or precursor for a bowel lumen for stenting (in) a bowel wall, for instance, in inflammatory bowel disease or Crohn's disease, for one or more segments within the bowel that are, e.g., ulcerated and/or in need of treatment. 42. The method of any of 1-39 comprising expanding a lumen before, during, or after placement of the material, e.g., gel, hydrogel, paste, or precursor. 43. The method of 42 comprising expanding the lumen with a balloon or a conventional stent (wire mesh, expandable stent, coronary artery stent, conventional vascular prosthesis). 44. The method of 43 comprising expanding the lumen and introducing the hydrogel, gel, paste, or precursor while the lumen is expanded, providing time for the hydrogel or other material to crosslink or otherwise gain mechanical strength, and removing the device used to expand the lumen, leaving the stenting material in place.

45. An injection device for injection into a tissue, for example a luminal wall, comprising a balloon catheter and an injection port for expelling a fluent material (e.g., gel, paste, hydrogel, or precursor) from the device into the luminal wall, with the balloon in fluid communication with a reservoir. Alternatively, an injection device for injection into a tissue, for example a luminal wall, comprising a helical or woven expandable tube (e.g., hydrotube) comprising an injection port for expelling fluent material (e.g., gel, paste, hydrogel, or precursor) from the device into the luminal wall. Alternatively, an injection device for injection into a tissue, for example a luminal wall, comprising a resilient curved needle and a pushing mandrel, e.g., with the needle disposed in a tube until positioned proximate the wall or other site and then pushed into the site with the pushing mandrel. 46. The device of 45 wherein the injection port is a hole. 47. The device of 45 wherein the injection port is a micro needle. 48. The device of any of 45-47 further comprising a tube adjacent to the balloon catheter wherein the tube comprises the injection port. 49. The device of 45 comprising the mandrel, wherein the pushing mandrel is flexible. 50. A method of using a device of any of 45-49 for injecting a gel, paste, hydrogel, or precursor, or a material of, or for the use of, any of 1-44.

51a. A stent for stenting a lumen that comprises the stent being made of a gel, paste, or hydrogel and being within the wall of an anatomical lumen, e.g., entirely within the wall. 51b. A luminal stent comprising a gel, hydrogel, or paste disposed entirely within a wall of a lumen. 52. For instance, the stent may be interior to the luminal surface, interior to an endothelial cell layer, interior to an intima, interior to a pseudointima, disposed in a space between the intima and the media, between the media and the adventitia, or being in the luminal wall. 53. The stent of 51 or 52 with the hydrogel being entirely within the tissue where it is placed and free of contact with fluids excepting fluids in, or of, the tissue. 54. The stent of 51 or 52 with the hydrogel being entirely within the wall and free of contact with the lumen and fluids in the lumen. 55. The stent of 51 or 52 wherein the stent is in a vascular wall and is interior to the adventitia and exterior to the intima. 56. The stent of any of 52-55 as placed by the method of any or 1-44, or comprising the gel, hydrogel, paste, or precursor of any of 1-44. 57. The stent of any of 52-55 being biodegradable or nonbiodegradable. 58. The stent of any of 52-55 wherein the stent comprises a therapeutic agent that is released from the stent. 59. The stent of any of 52-58 wherein the stent is a hydrogel and comprises the reaction product of a first precursor and a second precursor, with the first precursor and second precursor crosslinking with each other to form the hydrogel. 60. The stent of any of 52-59 wherein the stent, at the time of completing placement of the same at an intended site, has a height from about 0.1 mm to about 2 mm. Artisans will immediately appreciate that all ranges and values between the explicitly stated bounds are contemplated, with, e.g., any of the following being available as an upper or lower limit: 0.1, 0.2, 0.5, 1, 1.5, 1.9, 2. 61. The stent of any of 52-60 wherein the stent, at the time of completing placement of the same at an intended site, has a surface area sized from about 1 to about 150 mm$^2$. Artisans will immediately appreciate that all ranges and values between the explicitly stated bounds are contemplated, with, e.g., any of the following being available as an upper or lower limit: 1, 2, 3, 4, 5, 10, 20, 25, 30, 40, 50, 60, 80, 100, 125, 150. 62. The stent of any of 52-61 wherein the stent, at the time of completing placement of the same at an intended site, has a height from about 0.1 mm to about 2 mm and/or an area from about 10 to about 60 mm$^2$. Artisans will immediately appreciate that all ranges and values between the explicitly stated bounds are contemplated, with, e.g., any of the following being available as an upper or lower limit: 10, 12, 15, 20, 30, 40, 50, 55, 60. 63. The stent of any of 52-62 wherein the stent, at the time of completing placement at the intended site, has a volume of between about 1 µl and about 5 ml. Artisans will immediately appreciate that all ranges and values between the explicitly stated bounds are contemplated, with, e.g., any of the following being available as an upper or lower limit: 1, 5, 10, 100, 1000 microliters, 1.5, 2, 2.5, 3, 4, 5, ml. 64. The stent of any of 52-65 wherein the stent, at the time of completing placement of the same at an intended site, further comprises a plurality of particles that comprise the therapeutic agent. 65. The stent of any of 52-64 wherein the stent, is a low-swelling hydrogel, as measurable by the hydrogel having a weight increasing no more than about 50% upon exposure to a physiological solution for twenty-four hours relative to a weight of the hydrogel at the time of formation. 66. The stent of any of 52-65 wherein the stent is water-degradable, as measurable by the hydrogel being dissolvable in vitro in an excess of water by degradation of water-degradable groups. 67. The stent of any of 52-66 wherein the stent is a hydrogel and comprises the reaction product of formed by combining a first synthetic precursor comprising nucleophilic groups with a second synthetic precursor comprising electrophilic groups to form covalent crosslinks by reaction of the nucleophilic groups with the electrophilic groups to form the hydrogel. 68. The stent of 67 wherein the precursor is water soluble. 69. The stent of any of 52-68 with the stent comprising a therapeutic agent, wherein the therapeutic agent is selected from the group consisting of dexamethasone, nifedipine, a steroid, an inhibitor of vascular endothelial growth factor, an antiangiogenesis agent, a small molecule drug, a protein, a nucleic acid, and a growth factor. 70. The stent of any of 52-69 with the stent comprising a therapeutic agent, wherein the therapeutic agent is released over a period of time that is at least about three days. 71. The stent of any of 52-69 comprising a therapeutic agent, wherein a point at which a cumulative 80% w/w of the therapeutic agent has been released is reached at a time between about 14 days and 9 months. Artisans will immediately appreciate that all ranges and values between the explicitly stated bounds are contemplated, with, e.g., any of the following being available as an upper or lower limit: 2, 3, 4, 5, 6, 7, 8, 9, 10, 11, 12, weeks, 1, 2, 3, 4, 5, 6, 7, 8, 9 months. 72. A use of the stent of any of 52-71 as a stent for an anatomical lumen. 73. A use of the stent of 72 wherein the lumen is that of a ureter, blood vessel, vein, artery, aorta, an aneurysm, a brain aneurysm, an abdominal aortic aneurysm, or a cardiac blood vessel. 74. A use of the stent of 72 or 73 for a treatment of a stenosis or restenosis of veins, arteries, or a vascular structure; for urethral stenosis of benign prostate hyperplasia or a (benign or malignant) stricture of an esophagus; or for a bile duct occlusion. 75. A use of the stent 72 for stenting (in) a bowel wall, for instance, in inflammatory bowel disease or Crohn's disease, for one or more segments within the bowel that are, e.g., ulcerated and/or in need of treatment.

The invention claimed is:

1. A method of treating a luminal pathology affecting an anatomical lumen of a patient comprising
    injecting a precursor into a luminal wall of the anatomical lumen, and
    inflating a balloon in the anatomical lumen to expand the walls of the anatomical lumen,
    with the precursor reacting to form, in situ, a covalently crosslinked hydrogel stent within a luminal wall of the anatomical lumen with the hydrogel stent placed so that the hydrogel is free of contact with any fluids carried by the lumen.

2. The method of claim 1 wherein the precursor is in aqueous solution during the injecting into the luminal wall.

3. The method of claim 1 wherein the stent comprises a therapeutic agent that is released from the stent.

4. The method of claim 1 wherein the stent is biodegradable.

5. The method of claim 1 wherein the pathology is a stenosis or an aneurysm.

6. The method of claim 1 wherein the luminal wall is that of a blood vessel, ureter, vein, artery, aorta, bile duct, intestine, part of a gastrointestinal tract, esophagus, lymph duct, an aneurysm, a brain aneurysm, an abdominal aortic aneurysm, or a cardiac blood vessel, or a peripheral blood vessel.

7. The method of claim 1 wherein the luminal wall is that of a urethra, with the pathology being benign prostate hyperplasia.

8. The method of claim 1 further comprising injecting a free radical initiator with the precursor, with the initiator initiating polymerization of the precursor to form the hydrogel stent.

9. The method of claim 8 wherein the free radical initiator is thermal, photoactivatable, or a reduction-oxidation initiator.

10. The method of claim 8 wherein the free radical initiator is a thermal initiator that comprises a 4, 4' azobis (4-cyanopentanoic acid) group, a benzoyl peroxide group, or an analog of a benzoyl peroxide group.

11. The method of claim 8 wherein the free radical initiator comprises a peroxide group or a hydroperoxide group.

12. The method of claim 8 wherein the free radical initiator is a low temperature free radical initiator.

13. The method of claim 1 comprising an injection device for the injection, the device comprising a balloon catheter, a spiral tube, or a woven expandable tube, said device further comprising an injection port for expelling the one precursor from the device into the luminal wall.

14. The method of claim 13 wherein the device further comprising a resilient curved needle and a pushing mandrel.

15. The method of claim 13 wherein the injection port is a hole.

16. The method of claim 1 comprising an injection device for the injection, the device comprising a plurality of needles for the injecting.

17. The method of claim 1 wherein the stent being disposed within the luminal wall and also being disposed outside of the walls of the lumen.

18. The method of claim 1 wherein the stent is water degradable.

19. The method of claim 1 wherein the precursor is a first precursor that comprises an electrophilic functional group and further comprising injecting a second precursor comprising a nucleophilic group,
    wherein the hydrogel stent is a reaction product of an electrophilic-nucleophilic reaction between electrophilic functional groups of the first precursor and nucleophilic functional groups of the second precursor.

20. The method of claim 1 wherein the precursor is a hydrophilic polymer.

21. The method of claim 20 wherein the precursor comprises polyethylene glycol.

22. The method of claim 1 wherein the precursor is a free radical polymerizable polymer.

23. The method of claim 1 wherein the precursor is a first precursor and further comprising injecting a second precursor with the first precursor, wherein the second precursor is a hydrophilic molecule, with the first precursor and the second precursor covalently crosslinking to form the covalently crosslinked hydrogel stent.

* * * * *